(12) United States Patent
Okumura et al.

(10) Patent No.: US 10,194,861 B2
(45) Date of Patent: Feb. 5, 2019

(54) WIRED CIRCUIT BOARD

(71) Applicant: NITTO DENKO CORPORATION, Osaka (JP)

(72) Inventors: Keisuke Okumura, Osaka (JP); Eiji Toyoda, Osaka (JP); Shotaro Masuda, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/741,942

(22) PCT Filed: Jun. 1, 2016

(86) PCT No.: PCT/JP2016/066194
§ 371 (c)(1),
(2) Date: Jan. 4, 2018

(87) PCT Pub. No.: WO2017/006653
PCT Pub. Date: Dec. 1, 2017

(65) Prior Publication Data
US 2018/0192948 A1 Jul. 12, 2018

(30) Foreign Application Priority Data
Jul. 9, 2015 (JP) .................................. 2015-137963

(51) Int. Cl.
*H05K 1/00* (2006.01)
*A61B 5/00* (2006.01)
(Continued)

(52) U.S. Cl.
CPC ............. *A61B 5/6802* (2013.01); *H05K 1/02* (2013.01); *H05K 1/028* (2013.01); *H05K 1/189* (2013.01); *H05K 3/20* (2013.01); *H05K 3/22* (2013.01)

(58) Field of Classification Search
CPC ........ A61B 5/6802; H05K 1/02; H05K 1/028; H05K 1/189; H05K 3/20; H05K 3/22
See application file for complete search history.

(56) References Cited

U.S. PATENT DOCUMENTS 4,091,138 A * 5/1978 Takagi .................... C23C 14/02
148/DIG. 169
5,426,850 A * 6/1995 Fukutomi .............. H05K 3/205
29/847
(Continued)

FOREIGN PATENT DOCUMENTS

JP S57-2199 B2 1/1982
JP S57-4115 B2 1/1982
(Continued)

OTHER PUBLICATIONS

International Preliminary Report on Patentability issued by WIPO on Jan. 18, 2018, in connection with International Patent Application No. PCT/JP2016/066194.
(Continued)

*Primary Examiner* — Yuriy Semenenko
(74) *Attorney, Agent, or Firm* — Edwards Neils LLC; Jean C. Edwards, Esq.

(57) ABSTRACT

A wired circuit board includes an insulating layer and a conductive pattern embedded in the insulating layer. The conductive pattern has an exposed surface exposed from one surface in a thickness direction of the insulating layer and the insulating layer has the number of times of folding endurance measured in conformity with JIS P8115 (2001) of 10 times or more.

8 Claims, 4 Drawing Sheets

(51) Int. Cl.
*H05K 1/02* (2006.01)
*H05K 3/20* (2006.01)
*H05K 3/22* (2006.01)
*H05K 1/18* (2006.01)

(56) References Cited

U.S. PATENT DOCUMENTS

| | | | | |
|---|---|---|---|---|
| 5,527,998 | A * | 6/1996 | Anderson | H05K 3/361 174/254 |
| 8,552,299 | B2 * | 10/2013 | Rogers | H01L 21/4867 174/254 |
| 9,230,895 | B2 * | 1/2016 | Chou | H01L 21/4853 |
| 10,075,573 | B2 * | 9/2018 | Zhang | H01L 51/56 |
| 10,080,290 | B2 * | 9/2018 | Aleksov | H05K 1/184 |
| 2006/0231288 | A1 | 10/2006 | Vanfleteren et al. | |
| 2010/0065320 | A1 | 3/2010 | Urano | |
| 2018/0088500 | A1 * | 3/2018 | Mukoyama | G03G 15/2053 |

FOREIGN PATENT DOCUMENTS

| | | |
|---|---|---|
| JP | S60-176292 A | 9/1985 |
| JP | H05-299816 A | 11/1993 |
| JP | 2005-136318 A | 5/2005 |
| JP | 2011-014721 A | 1/2011 |
| JP | 2012-053050 A | 3/2012 |
| JP | 2013-146870 A | 8/2013 |
| JP | 2013-187380 A | 9/2013 |
| WO | 2008/069275 A1 | 6/2008 |

OTHER PUBLICATIONS

International Search Report Issued in PCT/JP2016/066194 dated Aug. 9, 2016.
Written Opinion Issued in PCT/JP2016/066194 dated Aug. 9, 2016.
Notification of Reasons for Refusal issued by the Japanese Patent Office dated Dec. 4, 2018, in connection with Japanese Patent Application No. 2015-137963.

* cited by examiner

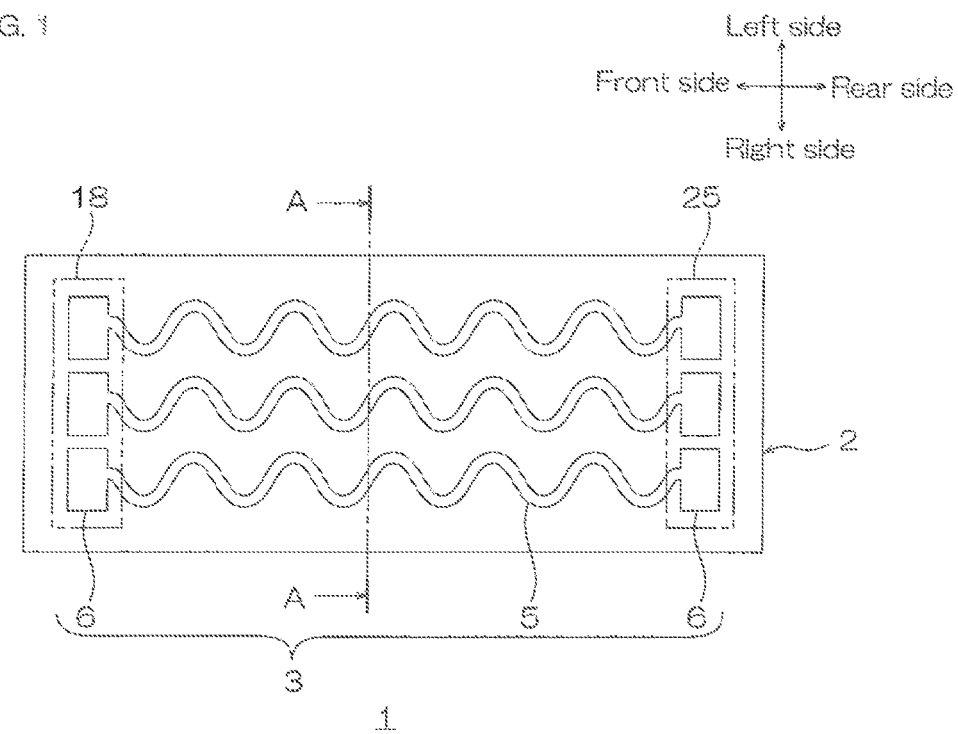
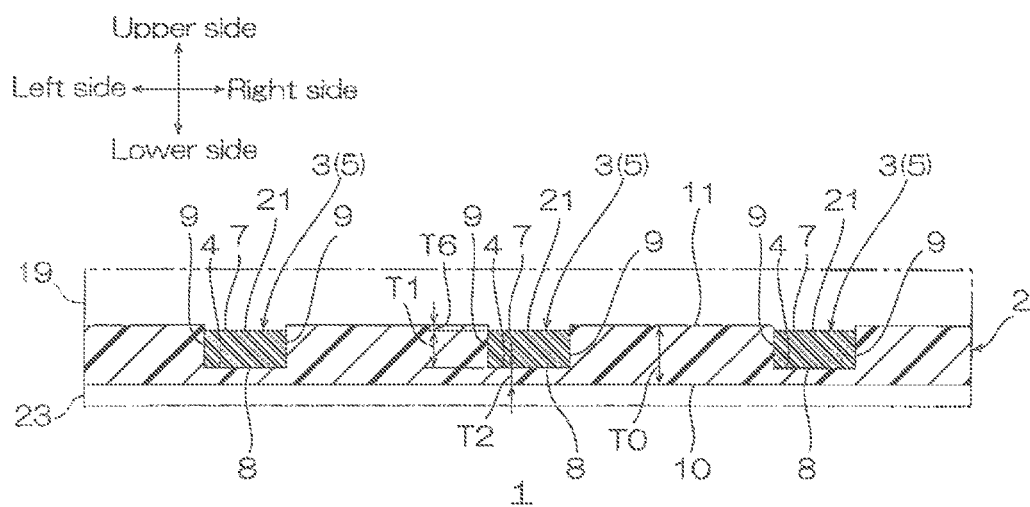

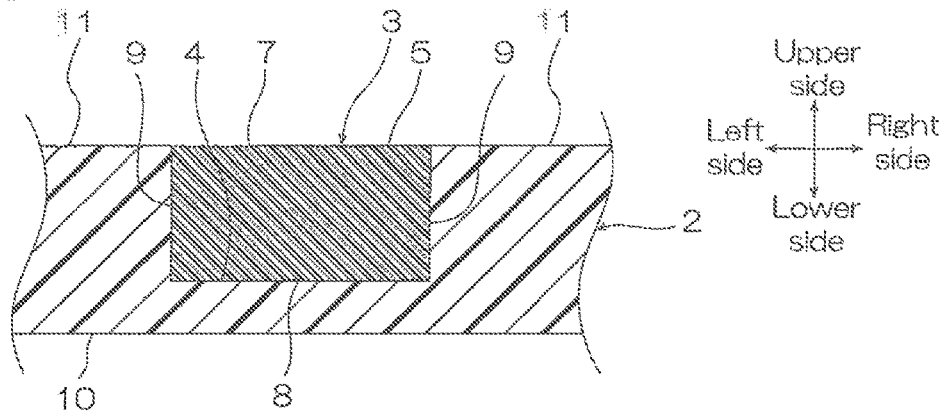
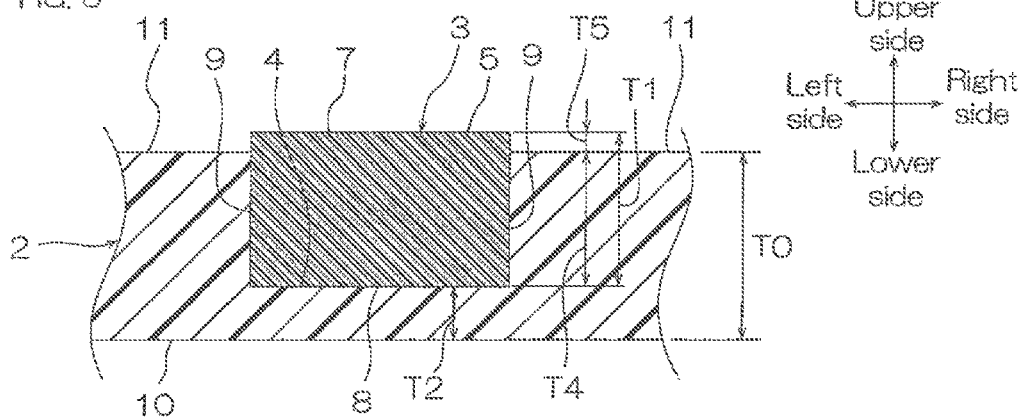
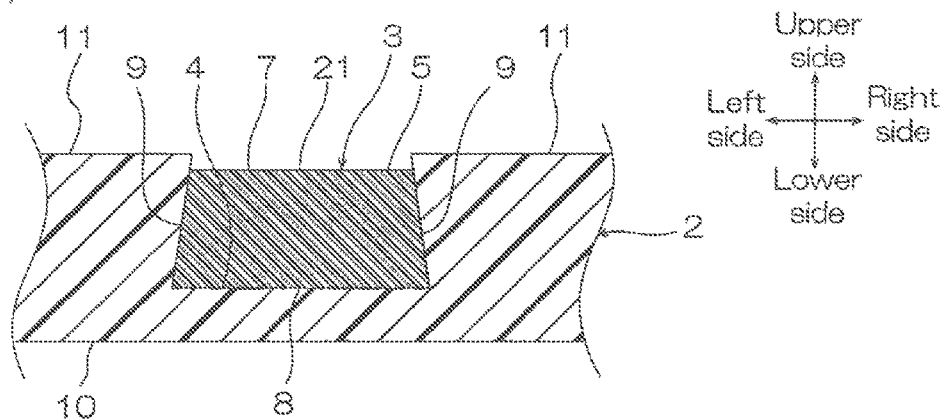

WIRED CIRCUIT BOARD

CROSS-REFERENCE TO RELATED APPLICATIONS

The present application is a 35 U.S.C. 371 National Stage Entry of PCT/JP2016/066194, filed on Jun. 1, 2016, which claims priority from Japanese Patent Application No. 2015-137963, filed on Jul. 9, 2015, the contents of all of which are herein incorporated by reference in their entirety.

TECHNICAL FIELD

The present invention relates to a wired circuit board and a wearable device, preferably, a wired circuit board and a wearable device including the wired circuit board.

BACKGROUND ART

A wearable device is used by being mounted on a part of the body or clothes of a user. Such a wearable device, for example, includes a wired circuit board so as to mount an electronic element for processing electric signals.

As such a wired circuit board, for example, an elastic flexible circuit board including an insulation base material made of a thermoplastic elastomer, a wiring layer formed on the insulation base material, and an insulation layer formed on the wiring layer and made of a thermoplastic elastomer has been proposed (ref: for example, Patent Document 1).

The elastic flexible circuit board described in Patent Document 1 is produced by first, forming the wiring layer on the insulation base material and thereafter, laminating the insulation layer on the insulation base material and the wiring layer.

CITATION LIST

Patent Document

Patent Document 1: Japanese Unexamined Patent Publication No. 2013-187380

SUMMARY OF THE INVENTION

Problem to be Solved by the Invention

A circuit board in which the wiring layer is formed on the insulation base material (that is, circuit board before laminating the insulation layer) may be produced and sold as an elastic flexible circuit board or a substrate thereof.

However, in such a circuit board, there is a disadvantage that the wiring layer is easily peeled from the insulation base material.

An object of the present invention is to provide a wired circuit board that is capable of suppressing the peeling of a conductive pattern from an insulation layer, and a wearable device.

Means for Solving the Problem

The present invention [1] includes a wired circuit board including an insulating layer and a conductive pattern embedded in the insulating layer, wherein the conductive pattern has an exposed surface exposed from one surface in a thickness direction of the insulating layer and the insulating layer has the number of times of folding endurance measured in conformity with JIS P8115 (2001) of 10 times or more.

According to the structure, the conductive pattern is embedded in the insulating layer, so that the conductive pattern is hard to be peeled from the insulating layer. Among all, the insulating layer has the number of times of folding endurance measured in conformity with JIS P8115 (2001) of the above-described lower limit or more, so that when the wired circuit board is expanded or contracted, the peeling of the conductive pattern from the insulating layer can be suppressed. Thus, the wired circuit board has excellent reliability.

The present invention [2] includes the wired circuit board described in the above-described [1], wherein the exposed surface of the conductive pattern is positioned so as to be flush with one surface in the thickness direction of the insulating layer or positioned at the other side in the thickness direction with respect to one surface in the thickness direction of the insulating layer.

According to the structure, a short circuit between the conductive patterns can be suppressed.

The present invention [3] includes the wired circuit board described in the above-described [2], wherein the exposed surface of the conductive pattern is positioned at the other side in the thickness direction with respect to one surface in the thickness direction of the insulating layer.

According to the structure, when the wired circuit board is produced by a roll-to-roll method and one surface in the thickness direction of the wired circuit board faces a roll, the contact area with the roll on one surface in the thickness direction of the wired circuit board can be reduced, while a gap between the exposed surface of the conductive pattern and the surface of the roll is provided. Thus, blocking of the wired circuit board with the roll can be suppressed.

The present invention [4] includes the wired circuit board described in the above-described [2] or [3], wherein the ratio (T1/T0) of a thickness T1 of the conductive pattern to a thickness T0 of the insulating layer is 0.05 or more.

According to the structure, the ratio of T1/T0 is the specified lower limit or more, so that thinning of the wired circuit board can be achieved.

The present invention [5] includes the wired circuit board described in any one of the above-described [2] to [4], wherein the thickness T1 of the conductive pattern is 1.0 μm or more.

According to the structure, the thickness T1 of the conductive pattern is the above-described lower limit or more, so that adhesive properties of the conductive pattern with respect to the insulating layer can be improved.

The present invention [6] includes the wired circuit board described in any one of the above-described [1] to [5], wherein the conductive pattern further has a facing surface that is disposed at the other side in the thickness direction facing the exposed surface at spaced intervals thereto and a connecting surface that connects the periphery end portion of the exposed surface to the periphery end portion of the facing surface, and the facing surface and the connecting surface are covered with the insulating layer.

According to the structure, the facing surface and the connecting surface are covered with the insulating layer, so that an adhesive force of the conductive pattern with respect to the insulating layer can be improved. Thus, the peeling of the conductive pattern from the insulating layer can be further more suppressed.

The present invention [7] includes the wired circuit board described in any one of the above-described [1] to [6], wherein a tensile storage elastic modulus E' at 20° C. at the time of subjecting the insulating layer to dynamic viscoelasticity measurement under the conditions of a frequency of 1 Hz and a temperature rising rate of 10° C./min is 1000 MPa or less.

According to the structure, the tensile storage elastic modulus E' of the insulating layer is the specified upper limit or less, so that the wired circuit board has excellent elastic properties.

The present invention [8] includes a wearable device including the wired circuit board described in any one of the above-described [1] to [7].

According to the structure, the wearable device includes the wired circuit board having excellent reliability, so that it has excellent reliability.

Effect of the Invention

The wired circuit board and the wearable device of the present invention have excellent reliability.

BRIEF DESCRIPTION OF THE DRAWINGS

FIG. 1 shows a plan view of one embodiment of a wired circuit board of the present invention.

FIG. 2 shows a cross-sectional view of the wired circuit board shown in FIG. 1 and a cross-sectional view in a right-left direction along an A-A line.

FIG. 3A illustrating a step (1) of forming a seed layer on the upper surface of a peeling layer, FIG. 3B illustrating a step of forming plating resists on the upper surface of the seed layer, FIG. 3C illustrating a step (2) of forming conductive patterns on the upper surface of the seed layer, FIG. 3D illustrating a step (3) of covering the seed layer and the conductive patterns with an insulating layer, FIG. 3E illustrating a step (4) of peeling the peeling layer from the seed layer, and FIG. 3F illustrating a step (5) of removing the seed layer.

FIG. 4A illustrating a state in which the wrist is not extended or bended,

FIG. 4B illustrating a state in which the wrist is extended, and

FIG. 4C illustrating a state in which the wrist is bended.

FIG. 5 shows an enlarged cross-sectional view of a wired circuit board (embodiment in which the upper surface of the conductive pattern is flush with the upper surface of the insulating layer) of a modified example of one embodiment.

FIG. 6 shows an enlarged cross-sectional view of a wired circuit board (embodiment in which the upper surface of the conductive pattern is positioned at the upper side with respect to the upper surface of the insulating layer) of a modified example of one embodiment.

FIG. 7 shows an enlarged cross-sectional view of a wired circuit board (embodiment in which the conductive pattern has a generally tapered shape when viewed in cross section) of a modified example of one embodiment.

DESCRIPTION OF EMBODIMENTS

In FIG. 2, the right-left direction of the paper surface is a right-left direction (first direction), the left side of the paper surface is a left side (one side in the first direction), and the right side of the paper surface is a right side (the other side in the first direction). In FIG. 2, the up-down direction of the paper surface is an up-down direction (second direction perpendicular to the first direction, thickness direction), the upper side of the paper surface is an upper side (one side in the second direction, one side in the thickness direction), and the lower side of the paper surface is a lower side (the other side in the second direction, the other side in the thickness direction). In FIG. 2, the depth direction of the paper surface is a front-rear direction (third direction perpendicular to the first direction and the second direction, longitudinal direction (ref: FIG. 1)), the near side of the paper surface is a front side (one side in the third direction, one side in the longitudinal direction), and the far side of the paper surface is a rear side (the other side in the third direction, the other side in the longitudinal direction). To be specific, the directions are in conformity with the direction arrows in each figure.

Figure 4A:
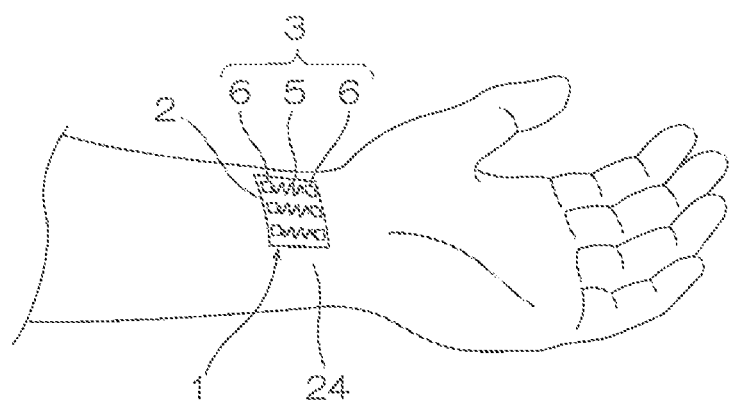
FIGS. 4A to 4C show embodiments in which a wearable device including the wired circuit board shown in FIG. 1 is attached to the skin of the inner-side portion of a wrist.
Figure 4B:
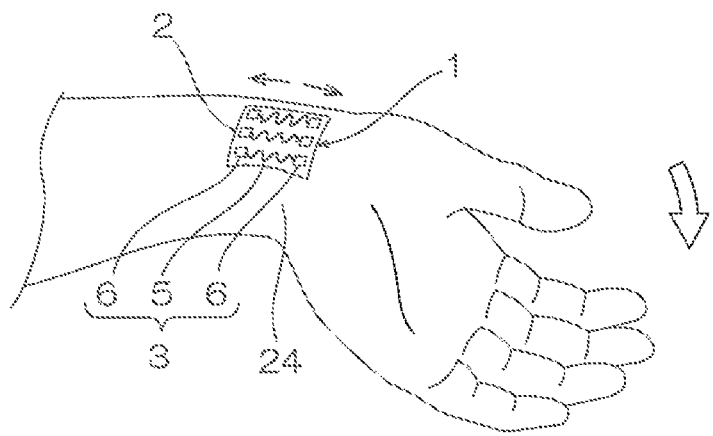
Figure 4C:
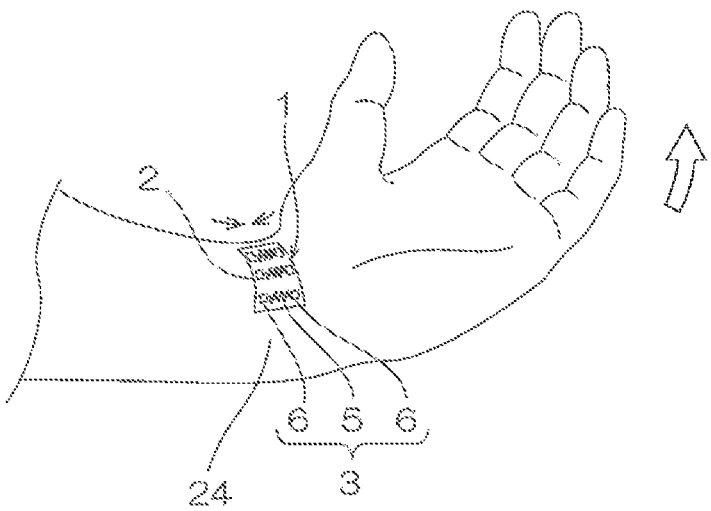

In FIGS. 4A to 4C, a sensor 18 and a memory 25 (described later) are omitted so as to clearly show the shape of a wired circuit board 1 (described later).

1. Wired Circuit Board

As shown in FIGS. 1 and 2, the wired circuit board 1 that is one embodiment of the present invention includes an insulating layer 2 and conductive patterns 3 that are embedded in the insulating layer 2.

1-1. Insulating Layer

As shown in FIG. 1, the insulating layer 2 has the same outer shape as that of the wired circuit board 1. To be specific, the insulating layer 2 has a film (sheet) shape in a generally rectangular shape when viewed from the top extending in the front-rear direction. As shown in FIG. 2, the insulating layer 2 includes a flat lower surface 10 and an upper surface 11 facing the upper side of the lower surface 10 at spaced intervals thereto. The insulating layer 2 includes a plurality of ditch portions 4 corresponding to the conductive patterns 3. Each of the plurality of ditch portions 4 has an opening upwardly.

The insulating layer 2 is, for example, formed of an insulating material that satisfies the number of times of folding endurance to be described later. Examples of the insulating material include polyurethane resin, (meth)acrylic resin (meaning acrylic resin and/or methacrylic resin, hereinafter, the same), urethane-(meth)acrylic resin, silicone resin, polyolefin resin (to be specific, polyethylene resin, polypropylene resin, or the like), polyvinyl chloride resin, polyvinylidene chloride resin, polyvinyl acetate resin, fluorine resin, styrene resin, butadiene resin, and isobutylene resin. The insulating materials can be used alone or in combination of two or more.

As the insulating material, in order to obtain characteristics of having both flexibility and toughness, preferably, polyurethane resin, (meth)acrylic resin, urethane-(meth)acrylic resin, and silicone resin are used, and in view of obtaining excellent folding endurance, more preferably, urethane-(meth)acrylic resin and silicone resin are used.

The urethane-(meth)acrylic resin is an ultraviolet curing resin, and is, for example, obtained by blending a material containing polyol, polyisocyanate, (meth)acrylic acid, and (meth)acrylate to be allowed to react under the presence of a photopolymerization initiator. To be specific, the above-described material and the above-described photopolymerization initiator are blended to prepare a mixture, and an ultraviolet ray is applied to the mixture to cure.

The silicone resin is a thermosetting resin, and examples thereof include polydimethyl siloxane, polymethylphenyl siloxane, and polydiphenyl siloxane. Preferably, polydimethyl siloxane is used.

The insulating layer 2 has the number of times of folding endurance measured in conformity with JIS P8115 (2001) of 10 times or more, preferably 100 times or more, more preferably, 1000 times or more, further more preferably, 10000 times or more and, for example, 100000 times or less. When the number of times of folding endurance of the insulating layer 2 is below the above-described lower limit, the peeling of the conductive pattern 3 from the insulating layer 2 cannot be suppressed at the time of repeatedly expanding or contracting the wired circuit board 1.

The details of the measurement method of the number of times of folding endurance of the insulating layer 2 are described in Examples later.

A tensile storage elastic modulus E' at 20° C. of the insulating layer 2 is, for example, 2000 MPa or less, preferably 1000 MPa or less, more preferably 100 MPa or less, further more preferably 50 MPa or less, particularly preferably 20 MPa or less, and for example, 0.1 MPa or more, preferably 0.5 MPa or more.

When the tensile storage elastic modulus E' of the insulating layer 2 is the above-described upper limit or less, excellent elastic properties of the insulating layer 2 can be ensured. Meanwhile, when the tensile storage elastic modulus E' of the insulating layer 2 is the above-described lower limit or more, excellent toughness and excellent handleability can be ensured.

The tensile storage elastic modulus E' at 20° C. of the insulating layer 2 is obtained by subjecting the insulating layer 2 to dynamic viscoelasticity measurement under the conditions of a frequency of 1 Hz and a temperature rising rate of 10° C./min.

A thickness T0 of the insulating layer 2 is, for example, 5 μm or more, preferably 10 μm or more, and for example, 1000 μm or less, preferably 300 μm or less.

As shown in FIG. 2, the thickness T0 of the insulating layer 2 is a distance T0 in the thickness direction between the lower surface 10 and the upper surface 11 of the insulating layer 2 in a region that is not overlapped with the conductive patterns 3 when projected in the thickness direction.

The thickness T0 of the insulating layer 2 is the same as the thickness of the wired circuit board 1.

1-2. Conductive Pattern

As shown in FIGS. 1 and 2, the conductive patterns 3 are disposed so as to be included in a projected surface of the insulating layer 2 when projected in the thickness direction. The conductive patterns 3 integrally include wires 5 extending in the front-rear direction and terminals 6 that are connected to both end portions in the front-rear direction of the wires 5.

The plurality of wires 5 are provided at spaced intervals to each other in the right-left direction. Each of the plurality of wires 5 has a generally wave shape (or sine wave shape).

The plurality of terminals 6 are provided in the front end portion and the rear end portion of the wired circuit board 1. Each of the plurality of terminals 6 is provided so as to be continuous to both end portions in the front-rear direction of the wires 5. Each of the plurality of terminals 6 is a land having a generally rectangular shape when viewed from the top.

As shown in FIG. 2, the conductive pattern 3 (to be specific, the wire 5) has a generally rectangular shape when viewed in cross section. To be specific, the conductive pattern 3 integrally has, as one example of an exposed surface, an upper surface 7, as one example of a facing surface, a lower surface 8 that is disposed at the lower side (one example of the other side in the thickness direction) facing the upper surface 7 at spaced intervals thereto, and as one example of a connecting surface, side surfaces 9 that connect the periphery end portion of the upper surface 7 to the periphery end portion of the lower surface 8. The conductive patterns 3 fit in the ditch portions 4 so as to be exposed from the upper surface 11 of the insulating layer 2.

The upper surface 7 of the conductive pattern 3 is positioned at the lower side (one example of the other side in the thickness direction) with respect to the upper surface 11 of the insulating layer 2. A step portion 21 with respect to the upper surface 11 of the insulating layer 2 is formed by the upper surface 7 of the conductive pattern 3 and the inner-side surfaces of the ditch portion 4 that are at the upper side with respect to the upper surface 7. The upper surface 7 of the conductive pattern 3 is a surface that is in parallel with the upper surface 11 of the insulating layer 2, and a flat surface extending in the front-rear direction. Furthermore, the upper surface 7 of the conductive pattern 3 is an exposed surface that is exposed from the upper surface 11 of the insulating layer 2.

The lower surface 8 of the conductive pattern 3 is a flat surface that is in parallel with the upper surface 7 of the conductive pattern 3. The lower surface 8 of the conductive pattern 3 is covered with the inner-side surfaces of the ditch portion 4 of the insulating layer 2. To be specific, the lower surface 8 of the conductive pattern 3 is in direct contact with the ditch portion 4 of the insulating layer 2.

The side surfaces 9 of the conductive pattern 3 are surfaces along the thickness direction (the up-down direction), and are covered with the inner-side surfaces of the ditch portion 4 of the insulating layer 2. The side surfaces 9 of the conductive pattern 3 are in direct contact with the ditch portion 4 of the insulating layer 2.

The conductive pattern 3 is, for example, formed of a conductive material such as copper, nickel, and gold or an alloy thereof. As the conductive material, preferably, copper is used.

The size of the conductive pattern 3 is appropriately set in accordance with its usages and purpose, and is not particularly limited. A length (width) in the right-left direction of each of the plurality of wires 5 is for example, 12 μm or more, preferably 15 μm or more, and for example, 1000 μm or less, preferably 750 μm or less. An interval between the wires 5 that are next to each other is, for example, 12 μm or more, preferably 15 μm or more, and for example, 10000 μm or less, preferably 7500 μm or less. A length (width) in the front-rear direction of each of the plurality of wires 5 is, for example, 10 mm or more, preferably 20 mm or more, and for example, 250 mm or less, preferably 100 mm or less. A length in the right-left direction and a length in the front-rear direction of each of the plurality of terminals 6 are, for example, 100 μm or more, preferably 200 μm or more, and for example, 10000 μm or less, preferably 5000 μm or less. An interval between the terminals 6 that are next to each other is, for example, 50 μm or more, preferably 100 μm or more, and for example, 10000 μm or less, preferably 5000 μm or less.

The ratio (S1/S0) of a plane area S1 (projected area when projected in the thickness direction) of the conductive pattern 3 to a plane area S0 of the insulating layer 2, that is, the ratio of the conductive pattern 3 to the insulating layer 2 when projected in the thickness direction is, for example, 70% or less, preferably 60% or less, and for example, 1% or more, preferably 3% or more. When the ratio of S1/S0 is the above-described upper limit or less, the wired circuit board 1 has excellent elastic properties.

A thickness T1 (distance T1 in the thickness direction between the upper surface 7 and the lower surface 8) of the conductive pattern 3, that is, the thickness T1 of each of the wires 5 and the terminals 6 is, for example, 0.3 μm or more, preferably 0.8 μm or more, more preferably 1.0 μm or more, and for example, 112 μm or less, preferably 75 μm or less, more preferably 40 μm or less. When the thickness T1 of the conductive pattern 3 is the above-described lower limit or more, an adhesive force of the conductive pattern 3 with respect to the insulating layer 2 can be improved, and the peeling of the conductive pattern 3 from the insulating layer 2 can be suppressed.

The ratio (T1/T0) of the thickness T1 of the conductive pattern 3 to the thickness T0 of the insulating layer 2 is, for example, below 1, preferably 0.9 or less, more preferably 0.8 or less, and for example, 0.05 or more, preferably 0.1 or more, more preferably 0.2 or more. When the ratio of T1/T0 is the above-described lower limit or more, thinning of the wired circuit board 1 can be achieved.

A thickness T2 of the insulating layer 2 that is positioned at the lower side of the conductive pattern 3, that is, the thickness T2 of the insulating layer 2 facing the conductive pattern 3 in the thickness direction is, for example, 200 μm or less, preferably 150 μm or less, more preferably 10 μm or less, and for example, 5 μm or more.

The ratio (T2/T0) of the thickness T2 of the insulating layer 2 that is positioned at the lower side of the conductive pattern 3 to the thickness T0 of the insulating layer 2 is, for example, 0.95 or less, preferably 0.85 or less, more preferably 0.75 or less, and for example, 0.1 or more. When the ratio of T2/T0 is the above-described upper limit or less, thinning of the wired circuit board 1 can be achieved, while an adhesive force of the conductive pattern 3 with respect to the insulating layer 2 is ensured.

The ratio (T1/T2) of the thickness T1 of the conductive pattern 3 to the thickness T2 of the insulating layer 2 that is positioned at the lower side of the conductive pattern 3 is, for example, 0.05 or more, preferably 0.1 or more, and for example, 0.9 or less, preferably 0.8 or less. When the ratio of T1/T2 is the above-described lower limit or more, thinning of the wired circuit board 1 can be achieved.

A distance T6 in the thickness direction between the upper surface 7 of the conductive pattern 3 and the upper surface 11 of the insulating layer 2, that is, a depth T6 of the above-described step portion 21 is, for example, 0.5 μm or more, preferably 1 μm or more, and for example, 10 μm or less, preferably 5 μm or less.

The ratio (T6/T0) of the depth T6 of the step portion 21 to the thickness T0 of the insulating layer 2 is, for example, 0.01 or more, preferably 0.03 or more, and for example, 0.5 or less, preferably 0.3 or less. When the ratio of T6/T0 is the above-described lower limit or more, the time to remove a seed layer 15 in a step (5) to be described later can be sufficiently ensured, so that a short circuit of the conductive patterns 3 that are next to each other via the seed layer 15 can be suppressed.

The sum (T1+T6) of the thickness T1 of the conductive pattern 3 and the depth T6 of the step portion 21 is a depth of the ditch portion 4, and is, for example, 1 μm or more, preferably 10 μm or more, and for example, 300 μm or less, preferably 100 μm or less.

The ratio ((T1+T6)/T0) of the depth (T1+T6) of the ditch portion 4 to the thickness T0 of the insulating layer 2 is, for example, 0.1 or more, preferably 0.2 or more, and for example, 0.9 or less, preferably 0.8 or less. When the above-described ratio is the above-described lower limit or more, thinning of the wired circuit board 1 can be achieved, while an adhesive force of the conductive pattern 3 with respect to the insulating layer 2 is ensured.

2. Method for Producing Wired Circuit Board

Next, a method for producing the wired circuit board 1 is described with reference to FIGS. 3A to 3F.

Figure 3A:
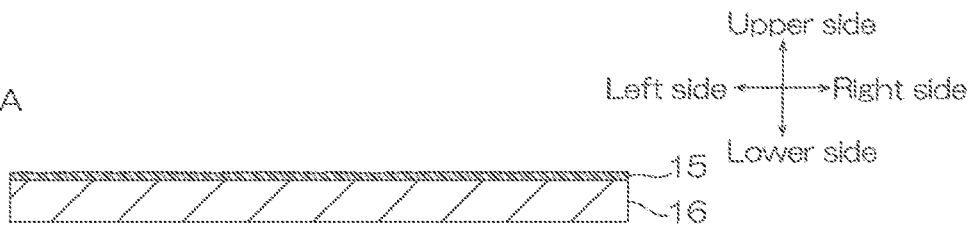
FIGS. 3A to 3F show process drawings for illustrating a method for producing the wired circuit board shown in FIG. 2.
Figure 3B:
Figure 3C:
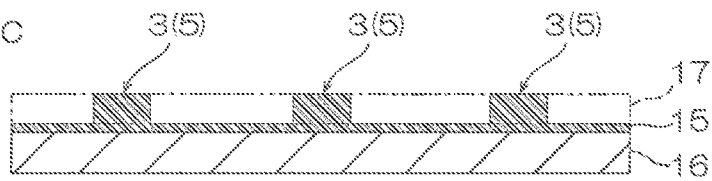
Figure 3D:
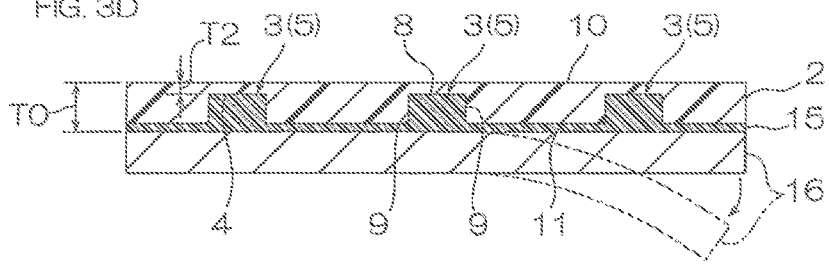
Figure 3E:
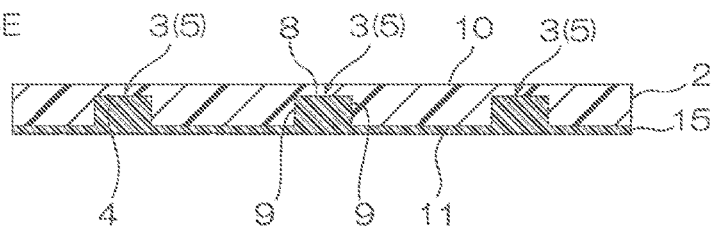
Figure 3F:
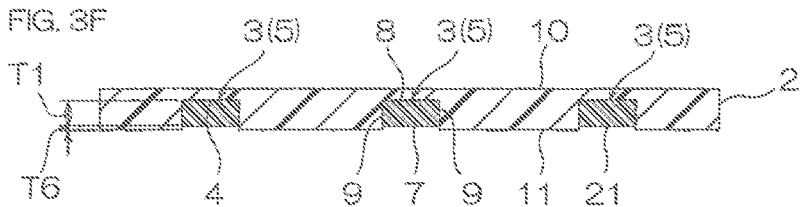

The producing method includes a step (1) of forming the seed layer 15 on the upper surface (one example of one surface in the thickness direction) of a peeling layer 16 (ref: FIG. 3A), a step (2) of forming the conductive patterns 3 on the upper surface (one example of one surface in the thickness direction) of the seed layer 15 (ref: FIGS. 3B and 3C), a step (3) of covering the seed layer 15 and the conductive patterns 3 with the insulating layer 2 (ref: FIG. 3D), a step (4) of peeling the peeling layer 16 from the seed layer 15 (ref: FIG. 3E), and a step (5) of removing the seed layer 15 (ref: FIG. 3F).

In the producing method, the wired circuit board 1 is, for example, produced by a roll-to-roll method or a single wafer (batch) method.

In the following, each of the steps is described.

2-1. Step (1)

In the step (1), as shown in FIG. 3A, the seed layer 15 is formed on the upper surface (one example of one surface in the thickness direction) of the peeling layer 16.

The seed layer 15 is, for example, formed of a metal material such as chromium, gold, silver, platinum, nickel, titanium, silicon, manganese, zirconium, and an alloy thereof or an oxide thereof. As the metal material, preferably, copper is used.

The peeling layer 16 is not particularly limited as long as it is a supporting layer capable of supporting the seed layer 15 and being peeled therefrom. Examples thereof include a resin layer and a metal layer. Preferably, a metal layer is used. The metal layer is, for example, formed from a metal material such as stainless steel, aluminum, and 42-alloy into a sheet shape. As the metal material, preferably, stainless steel is used. A thickness of the peeling layer 16 is, for example, 18 μm or more, preferably 30 μm or more, and for example, 200 μm or less, preferably 100 μm or less.

To form the seed layer 15 on the upper surface of the peeling layer 16, for example, a wet process such as plating and a dry process such as vacuum deposition and sputtering are used. The seed layer 15 is formed on the upper surface of the peeling layer 16 by preferably plating, more preferably, electrolytic plating.

The seed layer 15 is formed on the entire upper surface of the peeling layer 16.

A thickness of the seed layer 15 is, for example, 0.03 μm or more, preferably 0.3 μm or more, and for example, 5 μm or less, preferably 3 μm or less.

2-2. Step (2)

The step (2) is performed after the step (1). In the step (2), as shown in FIG. 3C, the conductive patterns 3 are formed on the upper surface of the seed layer 15.

As shown in FIGS. 3B and 3C, preferably, the conductive patterns 3 are formed on the upper surface of the seed layer 15 by an additive method.

To be specific, first, as shown in FIG. 3B, plating resists 17 are formed from a dry film resist on the upper surface of the seed layer 15 in a pattern reverse to the conductive patterns 3. Next, as shown in FIG. 3C, the conductive patterns 3 are laminated on portions that are exposed from the plating resists 17 on the upper surface of the seed layer

15 by electrolytic plating that supplies electricity from the seed layer 15. Thereafter, the plating resists 17 shown by phantom lines of FIG. 3C are, for example, removed by using a peeling solution.

The conductive patterns 3 have a shape continuous to the upper surface of the seed layer 15.

2-3. Step (3)

The step (3) is performed after the step (2). In the step (3), as shown in FIG. 3D, the seed layer 15 and the conductive patterns 3 are covered with the insulating layer 2.

For example, the insulating layer 2 made of a semi-solid or solid (to be more specific, B-stage) insulating material that is formed into a sheet shape in advance is prepared, and subsequently, the prepared insulating layer 2 is compressively bonded or transferred to the seed layer 15 and the conductive pattern 3. Or, a liquid (to be more specific, A-stage) insulating material (varnish or the like) is applied to the seed layer 15 and the conductive pattern 3.

Thereafter, when the semi-solid or solid insulating material, or the liquid insulating material is in an uncured state (A-stage state or B-stage state), the insulating material is allowed to cure (brought into a C-stage state) by ultraviolet irradiation or heating.

In this manner, the insulating layer 2 filling a space between the conductive patterns 3 and the outside of the conductive patterns 3 is formed on the upper surface of the seed layer 15 so as to cover the conductive patterns 3 and the seed layer 15. To be specific, the insulating layer 2 covers the upper surface of the seed layer 15, facing surfaces 8 of the conductive patterns 3 (in FIG. 3D, corresponding to the upper surfaces 8 and meanwhile, in FIG. 2, corresponding to the lower surfaces 8), and the side surfaces 9 thereof. In the insulating layer 2, the portions covering the facing surfaces 8 and the side surfaces 9 of the conductive patterns 3 are the ditch portions 4.

2-4. Step (4)

The step (4) is performed after the step (3). In the step (4), as shown in FIG. 3E, the peeling layer 16 is peeled from the seed layer 15.

To be specific, as shown by the phantom lines of FIG. 3D, the peeling layer 16 is peeled from the seed layer 15, while being deflected downwardly. For example, the right end portion of the peeling layer 16 is held and pulled downwardly so as to deflect the peeling layer 16 to be curved downwardly, so that the right end portion, the central portion in the right-left direction, and the left end portion of the peeling layer 16 are sequentially peeled from the right end portion, the central portion in the right-left direction, and the left end portion of the lower surface of the seed layer 15, respectively.

2-5. Step (5)

The step (5) is performed after the step (4). In the step (5), as shown in FIG. 3F, the seed layer 15 is removed.

The seed layer 15 is, for example, removed by etching such as wet etching.

Along with the removal of the seed layer 15, the lower end portions of the conductive patterns 3 filling the ditch portions 4 are removed. In this manner, the step portions 21 are formed. The thickness T6 of the lower end portion of the conductive pattern 3 that is removed is the same as the depth T6 of the step portion 21 described above.

The wired circuit board 1 shown in FIGS. 1 and 2 is obtained by the above-described steps (1) to (5).

3. Wearable Device

Next, a wearable device 20 including the above-described wired circuit board 1 is described.

As shown in FIG. 1, the wearable device 20 includes the wired circuit board 1, the sensor 18 (the phantom lines), and the memory 25 (the phantom lines).

As shown by the phantom lines of FIG. 2, a covering layer 19 and a pressure-sensitive adhesive layer 23 are provided in the wired circuit board 1 as needed. The covering layer 19 is formed on the upper surface 11 of the insulating layer 2 so as to cover the wires 5, and is formed of an insulating material or the like illustrated in the insulating layer 2. The pressure-sensitive adhesive layer 23 is provided on the lower surface of the insulating layer 2.

The sensor 18 is, for example, a measurement means capable of measuring data such as a pulse, a body temperature or the like of a user. The sensor 18 is electrically connected to the terminals 6 at the front end portion of the wired circuit board 1.

The memory 25 is a memory means capable of memorizing data measured by the sensor 18. The memory 25 is electrically connected to the terminals 6 at the rear end portion of the wired circuit board 1.

As shown in FIG. 4A, the wearable device 20 is, for example, attached to (mounted on) the skin of the inner-side portion of a wrist 24 of a user by the pressure-sensitive adhesive layer 23.

The wearable device 20 flexibly follows the extension of the wrist 24 (transfer to the back of the hand) as shown in FIG. 4B and the bending of the wrist 24 (transfer to the palm of the hand) as shown in FIG. 4C.

To be specific, as shown in FIG. 4B, the skin of the inner-side portion of the wrist 24 extends by the extension of the wrist 24, and following this movement, the wired circuit board 1 of the wearable device 20 extends.

Meanwhile, as shown in FIG. 4C, the skin of the inner-side portion of the wrist 24 bends by the bending of the wrist 24, and following this movement, the wired circuit board 1 of the wearable device 20 bends.

4. Function and Effect

In the wired circuit board 1, the conductive pattern 3 is embedded in the insulating layer 2, so that the conductive pattern 3 is hard to be peeled from the insulating layer 2. Among all, the insulating layer 2 has the number of times of folding endurance measured in conformity with JIS P8115 (2001) of the above-described lower limit or more, so that when the wired circuit board 1 is expanded or contracted, the peeling of the conductive pattern 3 from the insulating layer 2 can be suppressed. Thus, the wired circuit board 1 has excellent reliability.

When the ratio (T1/T0) of the thickness T1 of the conductive pattern 3 to the thickness T0 of the insulating layer 2 is the specified upper limit or less, thinning of the wired circuit board 1 can be achieved.

When the thickness T1 of the conductive pattern 3 is the above-described lower limit or more, adhesive properties of the conductive pattern 3 with respect to the insulating layer 2 can be improved.

According to the wired circuit board 1, the lower surface 8 and the side surface 9 are covered with the insulating layer 2, so that an adhesive force of the conductive pattern 3 with respect to the insulating layer 2 can be improved. Thus, the peeling of the conductive pattern 3 from the insulating layer 2 can be further more suppressed.

In the wired circuit board 1, when the tensile storage elastic modulus E' of the insulating layer 2 is the specified upper limit or less, the wired circuit board 1 has excellent elastic properties.

The wearable device 20 includes the wired circuit board 1 having excellent reliability, so that it has excellent reliability.

5. Modified Example

In the modified example, the same reference numerals are provided for members and steps corresponding to those described in one embodiment, and their detailed description is omitted.

In one embodiment, as shown in FIG. 2, the upper surface 7 of the conductive pattern 3 is positioned at the lower side with respect to the upper surface 11 of the insulating layer 2. Alternatively, for example, as shown in FIG. 5, the upper surface 7 of the conductive pattern 3 can be also positioned so as to be flush with the upper surface 11 of the insulating layer 2.

That is, as shown in FIG. 5, the upper surface 7 of the conductive pattern 3 and the upper surface 11 of the insulating layer 2 are positioned at the same position when projected in a plane direction (the front-rear direction and the right-left direction). In this manner, the upper surface 7 of the conductive pattern 3 and the upper surface 11 of the insulating layer 2 form a single flat surface. That is, the step portion 21 (ref: FIG. 2) in one embodiment is not formed on the upper surface of the wired circuit board 1.

To obtain the wired circuit board 1 shown in FIG. 5, in the step (5) (ref: FIG. 3F), the etching time is adjusted so that only the seed layer 15 is removed, and the lower end portions of the conductive patterns 3 filling the ditch portions 4 are not removed.

In the wired circuit board 1 shown in FIG. 5, the same function and effect as that of the wired circuit board 1 of one embodiment can be achieved.

Meanwhile, the wired circuit board 1 of one embodiment is preferable in view of suppressing blocking with the roll with respect to the wired circuit board 1 shown in FIG. 5.

That is, in the wired circuit board 1 of one embodiment shown in FIG. 2, when the wired circuit board 1 is produced by a roll-to-roll method and the upper surface of the wired circuit board 1 faces a roll (not shown), a gap (space) between the upper surface 7 of the conductive pattern 3 and the surface of the roll can be provided, which is different from the wired circuit board 1 shown in FIG. 5. Along with this, the contact area with the roll on the upper surface of the wired circuit board 1 can be reduced. Thus, blocking of the wired circuit board 1 of one embodiment shown in FIG. 2 with the roll can be suppressed, compared to the wired circuit board 1 shown in FIG. 5.

Meanwhile, as shown in FIG. 6, the upper surface 7 of the conductive pattern 3 can be also positioned at the upper side with respect to the upper surface 11 of the insulating layer 2.

In the wired circuit board 1 shown in FIG. 6, the lower end portion and the central portion of the conductive pattern 3 are embedded in the insulating layer 2, while the upper end portion thereof protrudes upwardly with respect to the upper surface 11 of the insulating layer 2.

An embedded depth T4 (that is, distance T4 in the thickness direction between the lower surface 8 of the conductive pattern 3 and the upper surface 11 of the insulating layer 2) of the conductive pattern 3, a protruding length T5 (that is, distance T5 in the thickness direction between the upper surface 7 of the conductive pattern 3 and the upper surface 11 of the insulating layer 2) of the conductive pattern 3, and the ratio (T4/T5) of the embedded depth T4 to the protruding length T5 of the conductive pattern 3 are appropriately set in accordance with its usages and purpose.

To obtain the wired circuit board 1 shown in FIG. 6, in the step (5) (ref: FIGS. 3E and 3F), first, a dry film resist (not shown) is laminated on the lower surface of the seed layer 15; next, an etching resist (not shown) having the same pattern as the conductive pattern 3 is formed from the dry film resist by exposure to light and development; and thereafter, only the seed layer 15 that is exposed from the etching resist is removed. Thereafter, the etching resist is removed.

In the wired circuit board 1 shown in FIG. 6, the same function and effect as that of the wired circuit board 1 shown in FIG. 2 in one embodiment can be achieved.

Meanwhile, in view of suppressing a short circuit between the conductive patterns 3, the wired circuit board 1 shown in FIGS. 2 and 5 is preferable, compared to the wired circuit board 1 shown in FIG. 6.

In the wired circuit board 1 shown in FIGS. 2 and 5, the upper surface 7 of the conductive pattern 3 is positioned at the lower side of or at the same position as the upper surface 11 of the insulating layer 2, which is different from the wired circuit board 1 shown in FIG. 6, so that a short circuit between the conductive patterns 3 can be suppressed.

In one embodiment, as shown in FIG. 2, the conductive pattern 3 has a generally rectangular shape when viewed in cross section. Alternatively, for example, as shown in FIG. 7, the conductive pattern 3 can also have a generally tapered shape when viewed in cross section.

In FIG. 7, the conductive pattern 3 has a generally tapered shape when viewed in cross section in which the length (width) in the right-left direction thereof gradually becomes short (narrow) toward the upper side.

That is, the side surfaces 9 that face each other in the right-left direction incline so as to gradually get close to each other toward the upper side.

The length (width) in the right-left direction of the lower surface 8 in the wire 5 with respect to the length (width) in the right-left direction of the upper surface 7 in the wire 5 is, for example, 101% or more, preferably 105% or more, and for example, 145% or less.

According to the wired circuit board 1 shown in FIG. 7, an adhesive force of the conductive pattern 3 with respect to the insulating layer 2 can be further more improved by an anchor effect of the conductive pattern 3 with respect to the insulating layer 2.

In one embodiment, as shown by the phantom lines of FIG. 2, the pressure-sensitive adhesive layer 23 is provided in the wired circuit board 1, and the insulating layer 2 is attached to the skin of the inner-side portion of the wrist 24 of the user via the pressure-sensitive adhesive layer 23. Alternatively, for example, the insulating layer 2 of the wired circuit board 1 can be also directly attached (bonded) to the skin of the inner-side portion of the wrist 24 of the user without providing the pressure-sensitive adhesive layer 23.

EXAMPLES

The specific numerical values in mixing ratio (content ratio), property value, and parameter used in the following description can be replaced with upper limit values (numerical values defined as "or less" or "below") or lower limit values (numerical values defined as "or more" or "above")

of corresponding numerical values in mixing ratio (content ratio), property value, and parameter described in the above-described "DESCRIPTION OF EMBODIMENTS".

Example 1

The peeling layer 16 made of stainless steel and having a thickness of 50 μm was prepared, and subsequently, the seed layer 15 made of copper and having a thickness of 1.0 μm was formed on the upper surface of the peeling layer 16 by electrolytic copper plating (the step (1), ref: FIG. 3A).

Next, a dry film resist was laminated on the entire upper surface of the seed layer 15 and next, the plating resists 17 were formed on the upper surface of the seed layer 15 in a pattern reverse to the conductive patterns 3 by exposing the dry film resist to light to be developed (ref: FIG. 3B). Next, the conductive patterns 3 made of copper and having a thickness of 3 μm were laminated on the upper surface of the seed layer 15 by electrolytic copper plating that supplied electricity from the seed layer 15. Thereafter, as shown in FIG. 3C, the plating resists 17 were removed by using a peeling solution (ref: the phantom lines of FIG. 3C, the step (2)).

A length in the right-left direction of each of the plurality of wires 5 was 50 μm and a length in the front-rear direction thereof was 60 mm. An interval between the wires 5 that were next to each other was 4050 μm. A length in the right-left direction and a length in the front-rear direction of each of the plurality of terminals 6 were 4000 μm. An interval between the terminals 6 that were next to each other was 100 μm. The plane area S1 of the conductive pattern 3 was 70 mm².

Separately, a varnish of a mixture (urethane-acrylic resin) prepared by formulations described in the "Details" column of "Insulating Material" described in Table 1 was applied to the seed layer 15 and the conductive pattern 3. Thereafter, the varnish in an A-stage state and B-stage state was allowed to cure (brought into a C-stage state) by applying an ultraviolet ray (irradiance: 340 mW/cm², amount of light: 4000 mJ/cm²) by using a high pressure mercury lamp, so that the insulating layer 2 was formed (the step (3), ref: FIG. 3D).

The thickness T0 of the insulating layer 2 was 10 μm. The thickness T2 of the insulating layer 2 facing the conductive pattern 3 was 7 μm. The depth of the ditch portion 4 was 3 μm. The ratio ((T1+T6)/T0) of the depth (corresponding to T1+T6 to be described later) of the ditch portion 4 to the thickness T0 of the insulating layer 2 was 0.3. The plane area S0 of the insulating layer 2 was 1600 mm², and the ratio of S1/S0 was 4.375%.

Next, the peeling layer 16 was peeled from the seed layer 15 (the step (4), ref: FIG. 3E).

Thereafter, the seed layer 15 was removed by wet etching (the step (5), ref: FIG. 3F). Furthermore, along with the removal of the seed layer 15, the lower end portions of the conductive patterns 3 filling the ditch portions 4 were removed.

The thickness T6 of the lower end portion of the conductive pattern 3 that was removed was 2 μm. The thickness T1 of the conductive pattern 3 was 1 μm. The ratio of T1/T2 was 0.143, the ratio of T6/T0 was 0.2, the ratio of T1/T0 was 0.1, and the ratio of T2/T0 was 0.7.

In this manner, the wired circuit board 1 including the insulating layer 2 and the conductive pattern 3 was obtained (ref: FIGS. 1 and 2).

Examples 2 to 7 and Comparative Examples 1 and 2

A wired circuit board 1 was obtained in the same manner as that of Example 1, except that the size and the arrangement of the conductive pattern 3, and the type, the details, and the curing conditions of the insulating material were changed in accordance with the descriptions in Table 1 (ref: FIGS. 2 and 6).

In Example 7, an etching resist was formed in the same pattern as that of the conductive pattern 3; thereafter, only the seed layer 15 that was exposed from the etching resist was removed; and then, the etching resist was removed. In this manner, in Example 6, the upper surface 7 of the conductive pattern 3 was positioned at the upper side with respect to the upper surface 11 of the insulating layer 2.

[Evaluation] The following items were evaluated. The results are shown in Table 1.

(1) Insulating Layer (1-1) Tensile Storage Elastic Modulus E'

The tensile storage elastic modulus E' at 20° C. of only each of the insulating layers 2 of Examples and Comparative Examples was measured by a dynamic viscoelasticity measurement method (DMA method) under the conditions of a temperature range of −10 to 260° C., a frequency of 1 Hz, and a temperature rising rate of 10° C./min.

(1-2) MIT Test (Folding Endurance)

The number of times of folding endurance of only each of the insulating layers 2 of Examples and Comparative Examples was counted by carrying out a MIT test (folding endurance test) under the following conditions in conformity with JIS P8115 (2001). Then, the folding endurance was evaluated in accordance with the following reference.

(Conditions)

Size of test piece: width of 15 mm, length of 110 mm

Test rate: 175 cpm

Bending angle: 135°

Load: 1.0 kgf

R of bending clamp: 0.38 mm

Opening of bending clamp: 0.25 mm (Reference)

Good: number of times of folding endurance of 10 times or more

Bad: number of times of folding endurance of below 10

(2) Wired Circuit Board (2-1) Adhesive Properties

A pressure-sensitive adhesive tape (No. 360UL, manufactured by NITTO DENKO CORPORATION) was attached to each of the upper surfaces of the wired circuit board 1 of Examples and Comparative Examples, and then, the pressure-sensitive adhesive tape was peeled from the wired circuit board 1. Subsequently, the movement of the above-described attachment and peeling was repeated. Then, the number of times required for peeling the conductive pattern 3 from the insulating layer 2 was obtained, and the adhesive properties were evaluated in accordance with the following reference.

Excellent: number of times of 3 or more

Good: number of times of 1 or 2

Poor: number of times of 0

(2-2) Short Circuit

A probe was touched to two wires that were electrically independent and next to each other, and a presence or absence of electrical conduction was checked based on resistance values of a digital multimeter by using a two-terminal resistance mode of a digital multimeter (ADVANTEST R6552 DIGITAL MULTIMETER).

A case where the electrical conduction was present, a short circuit between the wires was confirmed (short-circuited). A case where the electrical conduction was absent, a short circuit between the wires was not confirmed.

In the case of the presence of electrical conduction, some numerical value (numeral) was shown on a liquid crystal display portion of the digital multimeter.

In the case of the absence of electrical conduction, ".OL" (meaning OverLoad) was shown on a liquid crystal display portion of the digital multimeter.

TABLE 1

| | Ex. 1 | Ex. 2 | Ex. 3 | Ex. 4 | Ex. 5 | Ex. 6 | Ex. 7 | Comp. Ex. 1 | Comp. Ex. 2 |
|---|---|---|---|---|---|---|---|---|---|
| Corresponding FIG. | FIG. 2 | FIG. 2 | FIG. 2 | FIG. 2 | FIG. 2 | FIG. 2 | FIG. 6 | FIG. 2 | FIG. 2 |
| Thickness T1 of Conductive Pattern (μm) | 1 | 20 | 50 | 20 | 0.5 | 10 | — | 20 | 20 |
| Depth T6 of Step Portion (μm) | 2 | 5 | 10 | 5 | 0.5 | 10 | — | 5 | 5 |
| Thickness T0 of Insulating Layer (μm) | 10 | 100 | 200 | 100 | 10 | 200 | — | 100 | 100 |
| Thickness T2 of Insulating Layer Facing Conductive Pattern (μm) | 7 | 75 | 140 | 75 | 9 | 180 | — | 75 | 75 |
| T1/T0 | 0.1 | 0.2 | 0.25 | 0.2 | 0.05 | 0.05 | — | 0.2 | 0.2 |
| T2/T0 | 0.7 | 0.75 | 0.7 | 0.75 | 0.9 | 0.9 | — | 0.75 | 0.75 |
| T1/T2 | 0.143 | 0.267 | 0.357 | 0.267 | 0.056 | 0.056 | — | 0.267 | 0.267 |
| T6/T0 | 0.2 | 0.05 | 0.05 | 0.05 | 0.05 | 0.05 | — | 0.05 | 0.05 |
| (T1 + T6)/T0 | 0.3 | 0.25 | 0.3 | 0.25 | 0.1 | 0.1 | — | 0.25 | 0.25 |
| Insulating Material Type | | | | Silicone Resin | | | | Epoxy Resin | Prepreg |
| Insulating Material Details | Urethane-Acrylic Resin Mixture of 70 parts of Polytetramethylene Glycol (Manufactured by Mitsubishi Chemical Corporation, PTMG650), 25 parts of Xylylene Diisocyanate (Manufactured by Mitsui Chemicals, Inc., TAKENATE 500), 20 parts of Butyl Acrylate, 30 parts of Acrylic Acid, 50 parts of T-butyl Acrylate, and 0.3 parts of Photopolymerization Initiator (Manufactured by Ciba Specialty Chemicals, IRGACURE 2959) | | | Polydimethyl Siloxane (PDMS) (Manufactured by Shin-Etsu Chemical Co., Ltd, SIM-240) | Urethane-Acrylic Resin Mixture of 70 parts of Polytetramethylene Glycol (Manufactured by Mitsubishi Chemical Corporation, PTMG650), 25 parts of Xylylene Diisocyanate (Manufactured by Mitsui Chemicals, Inc., TAKENATE 500), 20 parts of Butyl Acrylate, 30 parts of Acrylic Acid, 50 parts of T-butyl Acrylate, and 0.3 parts of Photopolymerization Initiator (Manufactured by Ciba Specialty Chemicals, IRGACURE 2959) | | Mixture of Bisphenol A (BPA) Epoxy Resin (Manufactured by DIC, EPICLON 850S), MTHPA (Methyltetrahydrophthalic Anhydride), and Curing Accelerator (BDMA (Benzyl Dimethyl Amine)) | In Conformity with Japanese Unexamined Patent Publication No. 2010-80568 |
| Curing Conditions | Curing of Mixture by Applying Ultraviolet Ray (Irradiance: 340 mW/cm², amount of light: 4000 mJ/cm²) with High Pressure Mercury Lamp | | | Curing of PDMS by Heating at 150° C. for 3 hr | Curing of Mixture by Applying Ultraviolet Ray (Irradiance: 340 mW/cm², amount of light: 4000 mJ/cm²) with High Pressure Mercury Lamp | | | Curing of Mixture by Heating at 110° C. for 3 hr and 170° C. for 2 hr | In Conformity with Japanese Unexamined Patent Publication No. 2010-80568 |
| Evaluation Item — Insulating Layer — Tensile Storage Elastic Modulus E' [MPa] (20° C.) | 12 | 12 | | 1 | | 12 | | 3,000 | 20,000 |
| Wired Circuit Board — MIT Test (Folding Endurance) | Good | Good | Good | Good | Good | Good | Good | Bad | Bad |
| Adhesive Properties | Good | Excellent | Excellent | Excellent | Poor | Good | Excellent | Excellent | Excellent |
| Short Circuit | Absence | Absence | Absence | Absence | Absence | Absence | Presence | Absence | Absence |

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

The wired circuit board is used in the wearable device.

DESCRIPTION OF THE REFERENCE NUMERALS

1 Wired circuit board
2 Insulating layer
3 Conductive pattern
7 Upper surface (exposed surface)
8 Lower surface (facing surface)
9 Side surface (connecting surface)
11 Upper surface (insulating layer)
20 Wearable device
E' Tensile storage elastic modulus
T1 Thickness of conductive pattern
T0 Thickness of insulating layer

What is claimed is:

1. A wired circuit board comprising:
an insulating layer and
a conductive pattern embedded in the insulating layer, wherein
the conductive pattern has an exposed surface exposed from one surface in a thickness direction of the insulating layer and
the insulating layer has the number of times of folding endurance measured in conformity with JIS P8115 (2001) of 10 times or more.

2. The wired circuit board according to claim 1, wherein the exposed surface of the conductive pattern is positioned so as to be flush with one surface in the thickness direction of the insulating layer or positioned at the other side in the thickness direction with respect to one surface in the thickness direction of the insulating layer.

3. The wired circuit board according to claim 2, wherein the exposed surface of the conductive pattern is positioned at the other side in the thickness direction with respect to one surface in the thickness direction of the insulating layer.

4. The wired circuit board according to claim 2, wherein the ratio (T1/T0) of a thickness T1 of the conductive pattern to a thickness T0 of the insulating layer is 0.05 or more.

5. The wired circuit board according to claim 2, wherein the thickness T1 of the conductive pattern is 1.0 μm or more.

6. The wired circuit board according to claim 1, wherein the conductive pattern further has a facing surface that is disposed at the other side in the thickness direction facing the exposed surface at spaced intervals thereto and a connecting surface that connects the periphery end portion of the exposed surface to the periphery end portion of the facing surface, and
the facing surface and the connecting surface are covered with the insulating layer.

7. The wired circuit board according to claim 1, wherein a tensile storage elastic modulus E' at 20° C. at the time of subjecting the insulating layer to dynamic viscoelasticity measurement under the conditions of a frequency of 1 Hz and a temperature rising rate of 10° C./min is 1000 MPa or less.

8. A wearable device comprising the wired circuit board according to claim 1.

* * * * *